United States Patent [19]

Beiting

[11] Patent Number: 5,798,840
[45] Date of Patent: Aug. 25, 1998

[54] FAST OPTICAL ABSORPTION TOMOGRAPHY APPARATUS AND METHOD

[75] Inventor: Edward Joseph Beiting, Manhattan Beach, Calif.

[73] Assignee: The Aerospace Corporation, El Segundo, Calif.

[21] Appl. No.: 259,287

[22] Filed: Jun. 13, 1994

Related U.S. Application Data

[63] Continuation of Ser. No. 926,793, Aug. 5, 1992.

[51] Int. Cl.$^6$ .................................................. G01N 21/00
[52] U.S. Cl. ......................... 356/437; 356/435; 356/438
[58] Field of Search ............................. 356/432, 433, 356/434, 435, 436, 437, 438; 379/9

[56] References Cited

U.S. PATENT DOCUMENTS

| | | | |
|---|---|---|---|
| 4,057,725 | 11/1977 | Wagner | 378/9 |
| 4,386,854 | 6/1983 | Byer | 356/438 |
| 4,986,654 | 1/1991 | Meijer et al. | 356/43 |
| 5,178,002 | 1/1993 | Hanson | 356/315 |

OTHER PUBLICATIONS

Combustion Diagnostics by Multiangular Absorption, R. Goulard P. J. Emmerman Inverse Scattering Problems In Optics, Topics in Current Physics.

Laser Tomography for Simultaneous Concentration and Temperature Measurement in Reacting Flows, S. R. Ray, H. G. Semerjian Montreal, Canada, Jun. 1–3, 1983, pp. 300–324.

Optical Tomography in Combustion, R. Goulard, S. R. Ray Advances in Remote Sensing Retrieval Methods 1985, pp. 71–91.

Fan–Beam Tomography Noise Theory, K. E. Bennett, R. L. Byer Journal Optical Society of America, vol. 3, No. 5, May 1986, pp. 624–633.

Optical Tomography: Experimental Verification of Noise Theory K. Bennett & R. L. Byer Optics Letters, vol. 9, No. 7, Jul. 1984, pp. 270–272.

Experimental Optical Fan–Beam Tomography, K. E. Bennett, G. W. Faris R. L. Byer Applied Optics, vol. 23, No. 16, Aug. 15, 1984, pp. 2678–2685.

Quantitative Optical Tomographic Imaging of a Supersonic Jet G. W. Faris, R. L. Byer Optics Letters, vol. 11, No. 7, Jul. 1986, pp. 413–415.

High Speed Optical Tomography for Flow Visualization, R. Snyder, L. Hesselink, Applied Optics, vol. 24, No. 23, Dec. 1, 1985, pp. 4046–4051.

Long Optical Paths fo Large Aperture, J. U. White, Journal of Optical Society of America, vol. 32, May 1942, pp. 285–288.

Cavity Ring–Down Optical Spectrometer for Absorption Measurements Using Pulsed Laser Sources, A. O'Keefe and A. G. Deacon Rev. Sci Instrum. vol. 59, No. 12, Dec. 1988, pp. 2544–2551.

*Primary Examiner*—Richard A. Rosenberger
*Attorney, Agent, or Firm*—William J. Burke; Derrick M. Reid

[57] ABSTRACT

A design for a fast absorption optical tomography instrument is disclosed. The subject invention is capable of generating 100 projections of 100 elements each in less than 200 ns. It comprises and optical pulse generator, a tomography ring with temporally multiplexed fiber-optic fan-beam sources and fast detectors, and data acquisition electronics. A single short pulse (<10 ns) of radiation tuned to an absorption transition of the chemical species of interest produces a cross sectional image of concentration. Supplying two such pulses to the instrument can yield simultaneous quantitative images of temperature and absolute concentration in fields with temperature inhomogeneities. Additional pulses lead to concentration images of additional species.

10 Claims, 6 Drawing Sheets

FAST OPTICAL ABSORPTION TOMOGRAPHY APPARATUS AND METHOD

This is a continuation of copending application Ser. No. 07/926,793 filed on Aug. 5, 1992.

STATEMENT OF GOVERNMENT INTEREST

The invention described herein may be manufactured and used by or for the Government of the United States for governmental purposes without the payment of royalty therefor.

SUMMARY OF THE INVENTION

An absorption tomography instrument is constructed using an optical pulse generator, a tomography ring, and data acquisition electronics. The ring includes time-multiplexed, fiber-optic, fan-beam sources and fast, large area detectors. The fan-beam sources are sequentially activated in groups to minimize the number of detectors required to achieve a given resolution. The instrument is capable of acquiring 100 projections of 100 elements each, in less than 200 ns. The instrument can be tailored to particular application.

BACKGROUND OF THE INVENTION

1. Field of the Invention

This invention relates generally to techniques of visualizing planar fields of chemical concentration and/or temperature in rapidly moving gases and more particularly to the measurement of these quantities in turbulent flow.

2. Description of the Prior Art

The instantaneous three-dimensional characterization of reacting, turbulent flows is the ultimate goal of optical diagnostics of gases. Complete understanding of this environment requires simultaneous, spatially resolved measurements of both chemical and fluid dynamic parameters. Much progress toward this goal has been made using Rayleigh and Mie scattering. However, these scattering techniques cannot differentiate chemical species.

Planar laser induced fluorescence (PLIF) is the technique that competes most directly this proposed method because it is fast, capable of high spatial resolution, and can differentiate chemical species. FIG. 1A illustrates the difference in implementation between PLIF and optical absorption tomography. PLIF operates by crossing a flow of gas 2 with a sheet of light 4 tuned to an absorption of the chemical species of interest. A fraction of the molecules are excited from the ground state to an excited state of the molecule. PLIF images the emitted light 6 with an 2D detector 8 (electronic camera) and attempts to infer the magnitude of $N_0$ from this light. Tomography measures the amount of light absorbed across the sheet of light 4 using a one dimensional detector 10 creating a "projection." Projections must be measured at many angles around the flow and these data are used to "reconstruct" a cross sectional map of the concentration using computer algorithms.

PLIF suffers from collisional quenching that can render its measurements difficult to interpret quantitatively in practical flows. This is illustrated using FIG. 1B. Here, $N_0$ is the number of molecules in the ground state (concentration to be measured) and $N_1$ is the number of molecules excited by the laser radiation E. The number of molecules excited ($N_1$) exits this upper state via two channels: collisional de-excitation (quenching) Q and fluorescence F to an intermediate state in which light is emitted. The difficulty lies in the fact that the collisional deactivation rate Q generally is not known and this rate is many times larger than the deactivation rate due to fluorescence F (except in very low pressure flows). In optical absorption tomography the absorption depends only on $N_0$ and hence is independent of the unknown quenching rate Q.

Tomography was first suggested for the study of reacting flows by R. Goulard and P. J. Emmerman, Topics in Current Physics, 20; Inverse Scattering Problemns in Optics, H. P. Baltes, ed., Springer-Verlag, New York, p. 215, (1980). However, even though optical tomography can be applied to a wide class of important fluid dynamic problems, implementation has been limited to a few proof-of-principle studies. For example, R. Goulard and S. R. Ray, Advances in Remote Sensing Retrieval Methods, A. Deepak, H. E. Fleming, and M. T. Chahine, eds., A. Deepak Publishing, Hampton, Va. (1985) and S. R. Ray and H. G. Semerjian, Paper 83–1553, AIAA 18th Thermophysics Conference, Montreal, Canada (1983) have measured temperature and OH concentration fields in a steady-state, premixed flame with a continuous wave (cw) ring dye laser. Absorption experiments used fan beam geometry and either an $Ar^+$ laser through a rotating mirror to study an iodine plume (K. E. Bennett, G. W. Faris, and R. L. Byer, Appl. Opt. 22, 2678–2685 (1984); K. Bennett and R. L. Byer, Opt. Lett. 9, 270–272 (1984)) or a lamp source directed through a rotating chlorine jet (G. W. Faris and R. L. Byer, Opt. Lett 7, 413–415 (1986)) to create projections. More recently, R. Synder and L. Hesselink, Appl. Opt. 24, 4046–4051 (1985), demonstrated a novel configuration using holographic optical elements and a rotating mirror.

These studies share common shortcomings: they all rely on rotating elements and cw lasers, thus restricting measurements to a millisecond time scale. In order to be effective, a species-specific optical tomography instrument capable of imaging turbulent structure and temperature in fast reacting flows must collect data on a microsecond time scale.

The time resolution required of an instrument is determined by the necessity to freeze a resolution element. The size of the resolution element should approach the smallest space scale of the turbulence. For flow velocities not much greater than 100 m/s, the smallest space scale, or eddy, will be approximately 1 mm. If an element is considered to be stationary if it does not move more that 10% of its size during the measurement, all data must be collected in $10^{-6}$ s. As the velocity decreases and the scale size increases, this time increases considerably. Finally, about 10,000 pieces of data (pixels) should be collected during that time to create a meaningful image.

The primary object of this invention is therefore an absorption tomographic instrument capable of imaging one or more chemical species and/or temperature with sufficient temporal and spatial resolution to resolve turbulent structure in high speed gaseous flows. A related object of the invention is to capture nominally 100 projections of 100 elements each on a microsecond time scale.

DETAILED DESCRIPTION OF THE PREFERRED EMBODIMENT

Figure 1A:
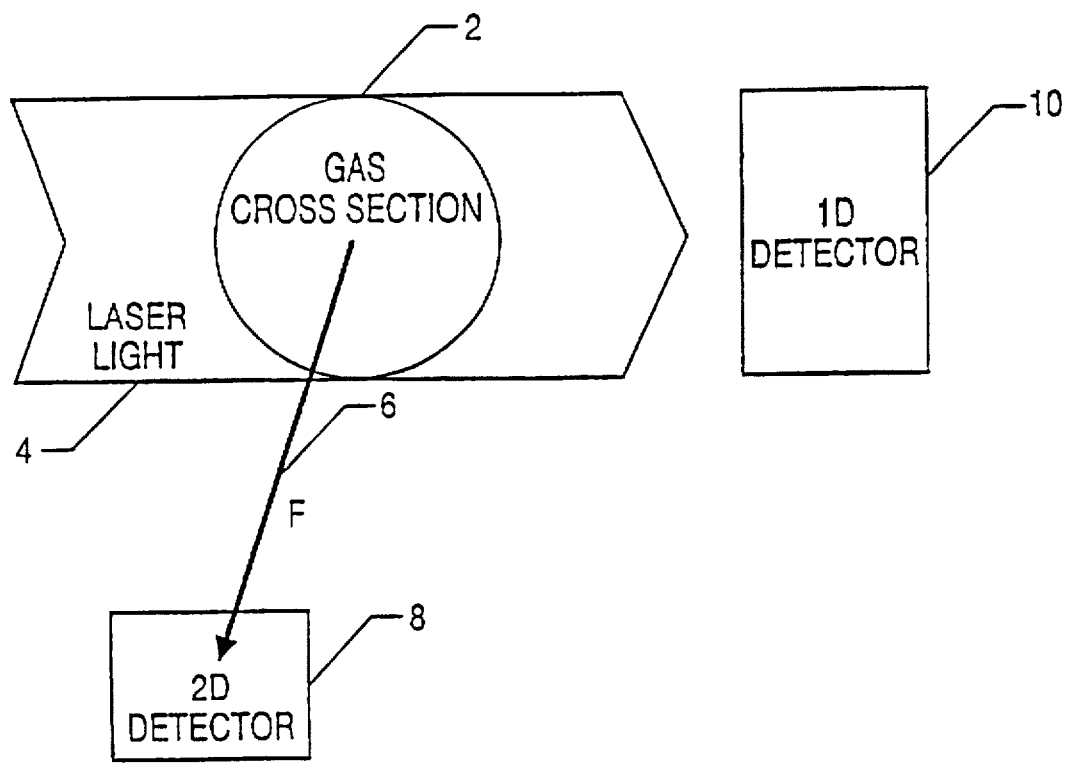
FIG. 1A and FIG. 1B illustrate the principles of planar laser induced fluorescence (PLIF) and absorption tomography.
Figure 1B:
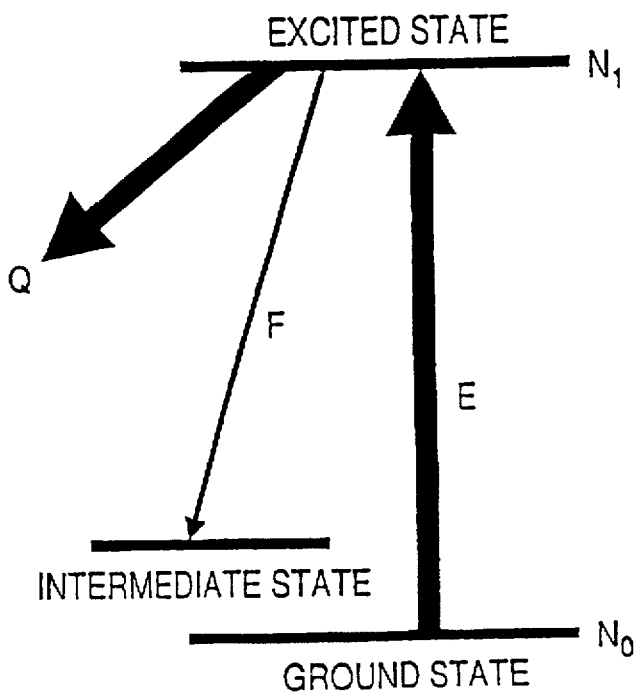
Figure 2:
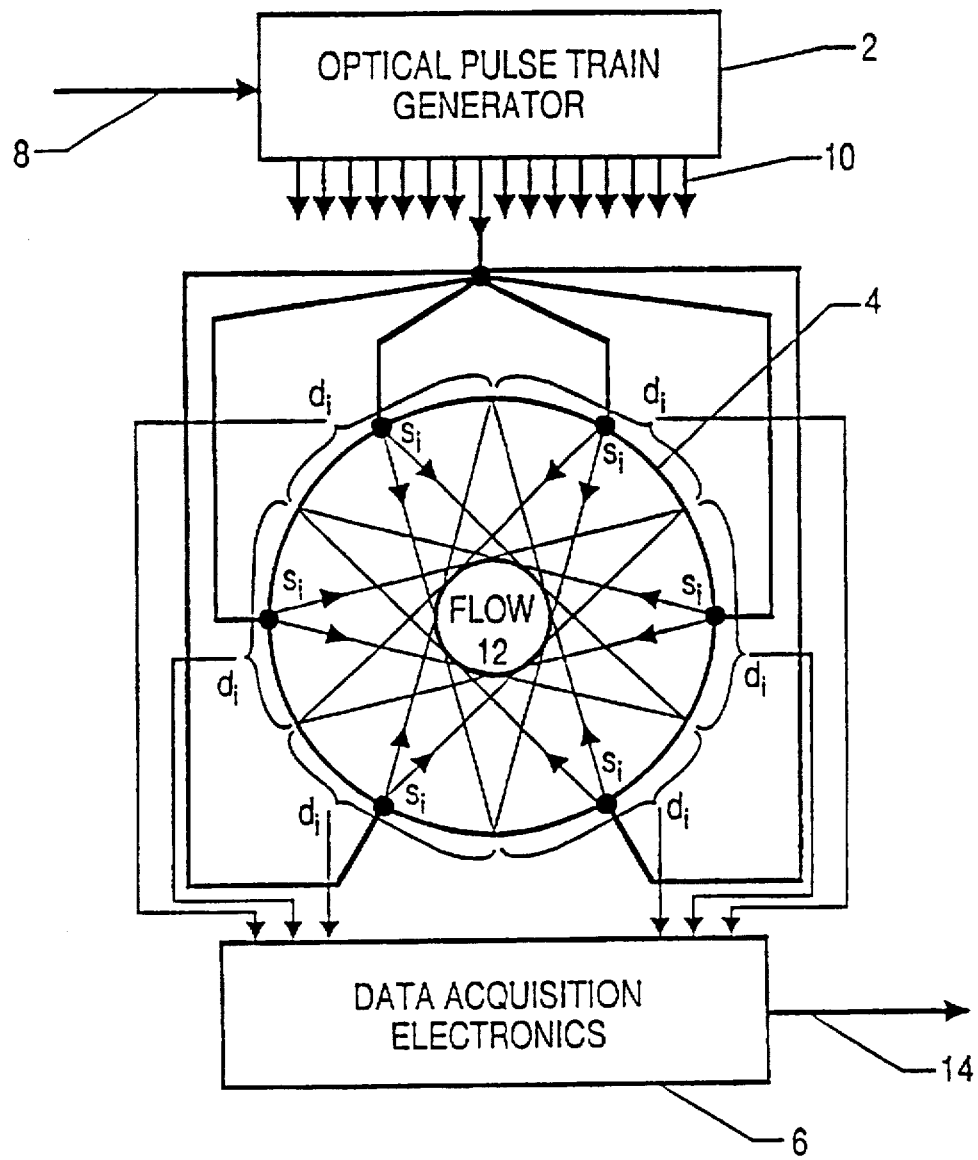
FIG. 2 shows the three principal components of the invention: an optical pulse train generator (OPTG); a tomography ring that surrounds the flow under investigation; and data acquisition electronics.

FIG. 2 illustrates the primary components of the invention. The invention comprises an optical pulse train generator (OPTG) 2, a tomography ring 4, and data acquisition electronics 6. In general, the OPTG 2 creates a series of n identical, equally spaced pulses from a single input laser pulse 8. For FIG. 2, n=16. Each pulse in the series is transmitted by means of a fiber-optic cable 10 that branches to m positions symmetrically placed around the tomography ring that surrounds a flow 12 under study. For FIG. 2, m=6. Each fiber optic is terminated with a microlens that casts the light into a flat fan. The fibers and microlenses thus create a total of n×m fan-beams sources $s_i$. Accordingly, sets of m fans are sequentially activated n times creating a total of n×m fans around the ring.

A series of detectors $d_i$ completely surrounding the flow is also located on the tomography ring 4 slightly above or below the fan beam sources. As each source $s_i$ illuminates the flow, the light is registered only by the detectors $d_i$ located on the opposite side of the ring in the path of the light from that fan. Information from the detectors is routed to the data acquisition electronics 6 in the form of a series of equally timed pulses of varying voltage. The electronics converts of the voltage pulses to numbers (i.e. digitizes them) using electronic sampling technology. The output data 14 are sent to a computer that reconstructs a cross-sectional view and displays it graphically. Each of the primary components is discussed in more detail below.

Optical Pulse Train Generator (OPTG) 2

The principle of the OPTG 2 is path-length delay and wavefront division. However, relaying even a well collimated laser beam between two plane retroreflectors and using a variable reflectivity beam splitter as an output coupler lead to impractical beam diameters and inconvenient path lengths after a few pulses. The device introduced here, based on the stable geometry of a White cell [J. U. White, J. Opt. Soc. Am. 32, 285–288 (1942)], avoids these problems.

Figure 3:
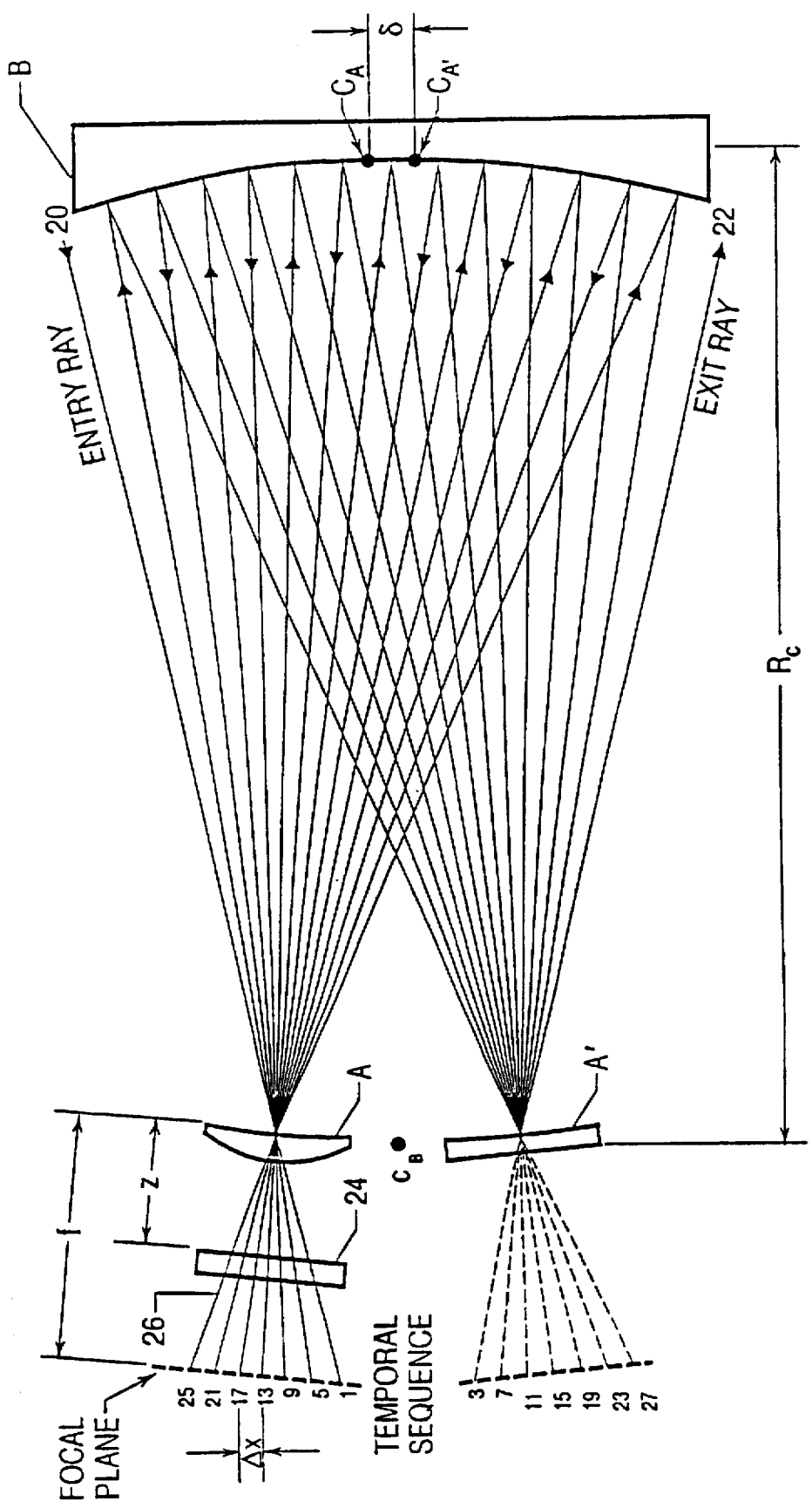
FIG. 3 shows the geometry used to generate a series of pulses separated by equal time intervals.

FIG. 3 illustrates a modified White cell. A classical White cell comprises entrance 20 and exit 22 slits, and three spherical mirrors A,A' and B, with equal radii of curvature, $R_c$. The slits 20, 22 lie at opposite edges of mirror B, a distance $R_c$ from $C_B$, its center of curvature. The centers of curvature of mirrors A and A' lie symmetrically about the center of mirror B at points $C_A$ and $C_{A'}$. Light diverging from the entrance slit 20 is collected and focused by mirror A to position 2 on the surface of mirror B. This light then diverges to mirror A', which focuses it to position 4 on the surface of mirror B, etc. The conjugate object and image rays striking mirror A (or A') make equal angles with the line joining the center of mirror A (or A') with $C_A$ (or $C_{A'}$). The focal points on mirror B are separated by the distance between the centers of curvature, $\delta = \overline{C_A C_{A'}}$. Symmetrically pivoting and reducing the separation between mirrors A and A' to decrease the separation $\delta$ increases the number of traverses through the cell. The entrance slit must be placed a distance $(n+\frac{1}{2})\delta$ from $C_A$ (where n is an integer) to have the final beam pass through a symmetrically placed exit slit. Placing the entrance slit a distance $n\delta$ from $C_A$ results in ray positions on mirror B separated by $2\delta$ as the ray retraces itself along the same paths in the opposite direction.

To use this geometry for the OPTG 2, the entrance and exit slits are eliminated and the output of a laser is introduced directly at the entrance slit position. Although the divergence of the beam is not critical, the beam will be considered to be reasonably collimated in the following discussion. The diameter of mirrors A and A' and the height of mirror B need only be large enough to accommodate the beam diameter. All beams traveling toward mirrors A and A' are collimated (i.e., have the divergence of the original beam). All beams traveling to mirror B converge to waists located near the center of the cell and subsequently diverge to mirror B. This geometry can produce a train of equally spaced pulses because the sum of the optical paths of any pair of left and right traveling beams always equals $2R_c$. Therefore, beams at the surface of mirror B are temporally separated by multiples of $2R_c/c$ and those on mirrors A and A' are separated by multiples of $4R_c/c$, where c is the speed of light. Note that this configuration is useful for high power laser applications since the beam waists are near the center of the cell, minimizing the intensity at the surface of the mirrors.

Although any or all of the mirrors can be used as output couplers, it is particularly convenient to use mirror A to extract the train of pulses. The concave face of mirror A is uniformly covered with a partially reflecting coating; the back is given a radius of curvature shorter than that of its reflecting surface to create a positive meniscus lens of focal length $f$. The collimated beams passing through this output coupler form a fan of beams that are individually focused along a straight line a distance $f$ behind mirror A. The total number of points (pulses), in this line is $$n_p = \frac{L_B + \delta}{2\delta} \quad (1)$$

where $L_B$ is the length of mirror B. The maximum number of pulses, $n_p^{max}$, that can exit this output coupler is $L_B/d$ where d is the diameter of the entry beam. The foci are separated at the focal plane by $$\Delta x_{focus} = 2f\delta/R = \frac{4R_o\delta}{R_c + R_o} \quad (2)$$

where $R_o$ is the radius of curvature of the outer surface of the output coupler A.

The amplitudes of the pulses exiting the output coupler A are not constant and are a strong function of the reflectivities. If $r_A$, $r_B$, and $r_{A'}$ are the reflectivities of mirrors A, B, and A', respectively, then the fractional decrease in amplitude from pulse-to-pulse is $$\frac{I_i - I_{i+1}}{I_i} = 1 - r_A r_B^2 r_{A'} \quad (3)$$

where $I_i$ is the amplitude of the ith pulse. The ratio of the amplitude of the last-to-first pulse for a train of $n_p$ pulses is $(r_A r_B^2 r_{A'})^{n_p+1}$. If the entrance pulse has an amplitude of $I_0$, then the efficiency of the OPTG is $$\sum_{i=1}^{n_p} I_i/I_0 = (1-r_A) \left[ \frac{1-(r_A r_B^2 r_{A'})^{n_p}}{1-r_A r_B^2 r_{A'}} \right]. \quad (4)$$

These expressions assume the absorption and scatter of the output coupler are negligible.

A train of pulses of equal amplitude can be obtained at the expense of efficiency by inserting a variable neutral density filter 24 in the fan 26 of output beams. For constant spacing, $\Delta x$, between the adjacent outputs, the constraint that all transmitted amplitudes be equal leads to an expression for the optical density of the filter that is linear in position with a slope of $\log(r_A r_B^2 r_{A'})/\Delta x$. Accordingly, a train of pulses of equal amplitude can be produced by inserting a standard variable neutral density filter 24 normal to the central ray 13 of the output fan 26. Adjusting the distance z of the filter from the output coupler A selects the proper slope, and adjusting its position normal to the central ray 13 selects the correct intercept.

Tomography Ring 4

Figure 4:
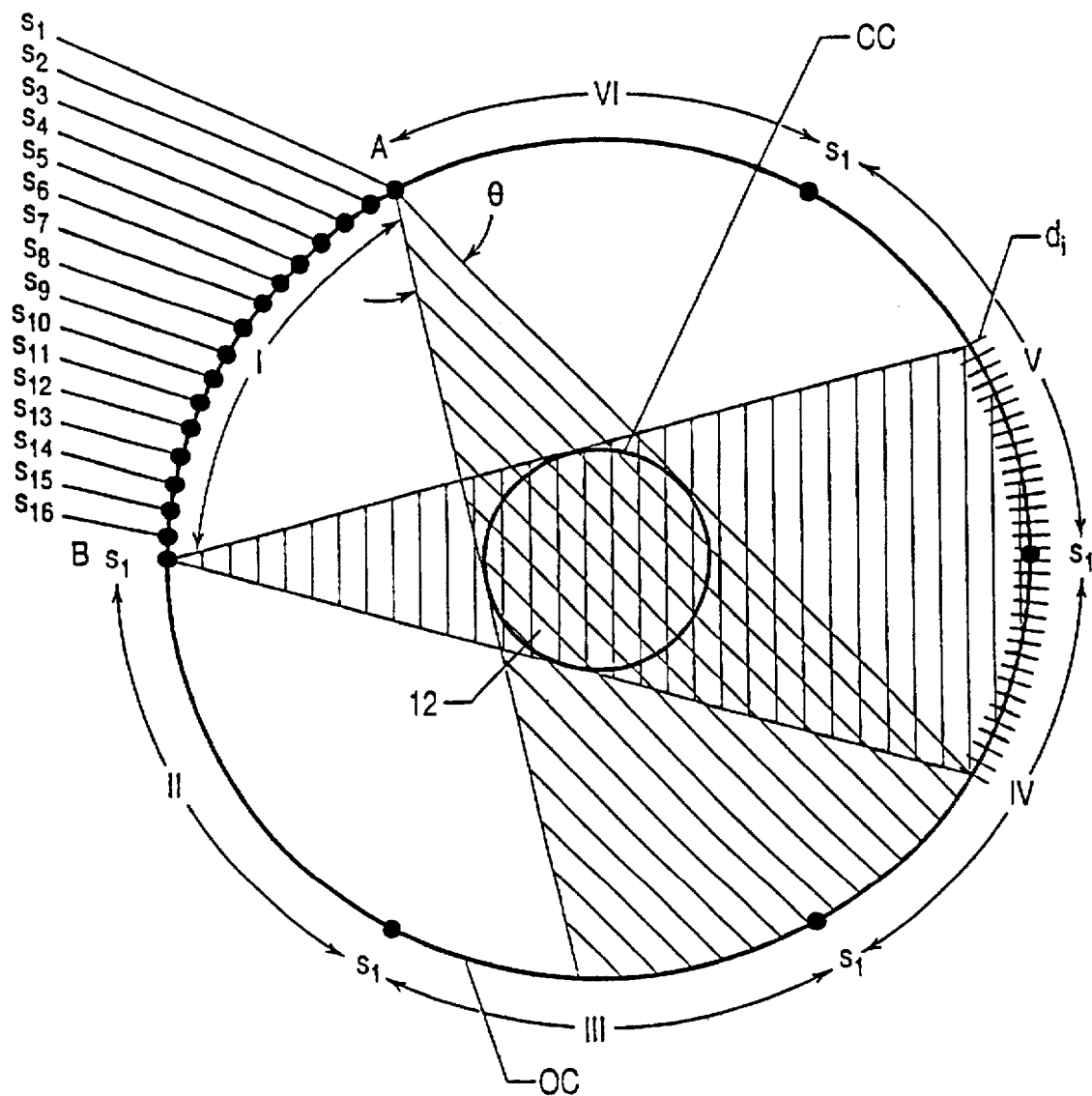
FIG. 4 is a schematic illustration a 96-fiber, 16 times multiplexing implementation of the instrument.

FIG. 4 illustrates the geometry of the tomography ring. The center circle CC represents the cross section of the flow 12 to be investigated. The circumference of the outer circle 12 describes a locus of point sources organized into separate sectors I, II ... Each source $s_i$ consists of a diverging flat fan of light of angle $\theta$. The rays from each source pass through the probed region 12 and terminate on a series of detectors $d_i$ also located on the outer circle OC. If the sources are separated by $\geq 2\theta$ (fans A and B), rays from their fans will not overlap on the opposite side of the circle, and a one-to-$n_d$ correspondence exists between the sources and detectors, where $n_d$ is the number of detectors in each fan.

FIG. 4 depicts a geometry where six equally spaced fan sources $s_i$ could illuminate the entire circle of detectors $d_i$ without overlap. Now, consider placing fifteen additional sources $s_2 - s_{16}$ in section I. Further, consider that these sources are activated sequentially so that source $s_1$ is emitting a fan of radiation at time $t_1$, source $s_2$ is emitting a fan of radiation at time $t_2$, etc., and that the time interval between each pulse of radiation is greater than the time any source is active. Then, a detector $d_i$ will receive the radiation from only one source at a time.

A train of these radiation pulses equally spaced in time is created from a single laser pulse 8 using the optical pulse train generator 2. Now consider that each pulse exiting the OPTG 2 is split so that it is carried to a source in sectors I-VI. This splitting is done effectively using fused fiber splitters (star couplers). Thus, the first pulse from the train is coupled to six fibers that carry the simultaneous pulses to the six locations marked $s_1$ on the circumference of the outer circle OC. The next pulse creates fans at the six $s_2$ locations, etc. In this way, 96 sources are created, but only 6 widely separated sources are active at any instant. In this example, 96 sources each illuminate 96 detectors, but only a total of 6×96=576 detectors is required. If the time interval between the pulses is 12 ns, the entire sequence is completed in 16×12 ns=196 ns.

More generally, the source ring radius required to fully sample a flow of radius $r_f$ is $$R = r_f \sqrt{2/(1-\cos\theta_{fan})} \equiv F r_f, \quad (5)$$

where the fan angle is $$\theta_{fan} = \frac{\pi F_M}{N_f}, \quad (6)$$

$r_f$ is the radius of the flow cross section, $F=R/r_f$, $N_a$ ($=\pi/\theta_{fan}$) is the number of sectors (I,II ... ), $N_f=N_a F_M$ is the total number of fan sources, and $F_M$ is the multiplexing factor (equal to 16 in the example above).

The spatial resolution of the instrument is approximately one-half the detector spacing if the detectors and sources reside on the same ring and the cross section is not under sampled in angular space. The total number of detectors, $N_d$, necessary as a function of detector spacing, $\omega$, is $$N_d = \frac{2\pi r_f F}{w} = \frac{4 r_f N_f}{w F_M}, \quad (7)$$

where F is defined by Eq. (5) and the approximation holds for small fan angles. Thus, the total number of detectors scales inversely with the multiplexing factor.

The multiple use of each detector allows a large number of equally spaced projections to be acquired while maintaining a large detector size. The width of the detectors is chosen to equal the detector spacing. There are several compelling reasons for using as large a detector size as possible consistent with the desired spatial resolution. These include increasing the signal-to-noise ratio and reducing the deleterious effects of diffraction, turbulence-induced beam steering, and laser speckle noise. Although reconstruction algorithms assume point detectors, the finite detector size does little to introduce artifacts into the reconstruction when algorithms based on the Radon operator are used in the backprojection algorithm to calculate the cross section of the flow.

From Eqs. (5–7), an expression for the width w available for the detector is found to be $$w = \frac{2\pi r_f}{N_a n_d} \sqrt{2/(1-\cos(\pi/N_a))}. \quad (8)$$

Note that, for a single source-detector ring and a given resolution, the flow diameter dictates the detector spacing. If this is inconvenient for the size of the available detectors, the fan sources and detectors can be placed on separate concentric rings with different diameters. Higher spatial resolution for a given detector size can always be obtained by increasing the ratio of the detector-ring radius to fan-ring radius Data Acquisition and Output Electronics 6

It is necessary to individually digitize the amount of charge exiting each pulse in each detector. However, if the shape of each pulse is identical, then the peak amplitude or voltage of each pulse is directly proportion to the charge of the pulse. Since all pulses created by the OPTG 2 are derived from the same laser pulse 8, all pulse shapes are identical. Although flash digitizers are available that can digitize pulses on a nanosecond time scale, they are expensive and have only 8 bit resolution. A more practical method to digitize the train of pulses emitted from each detector $d_i$ is to use fast sampling techniques and analog shift registers. Here, the peak of each pulse is sampled (the voltage sensed) and rapidly stored in one of a series of capacitors etched in a monolithic integrated circuit (IC). Since all the pulses are equally spaced in time, a single clock (pulse generator) is used to synchronize and set the sampling rate to the pulse rate. The information is collected and stored in the capacitors on a nanosecond times scale but is read out and digitized on a millisecond time scale, thus allowing high resolution (12 bit) digitization. Current technology allows 128 pulses from each of 32 different detectors to be processed by a single IC.

These digitized values (numbers) are rapidly stored in the memory of the computer controlling the instrument. The numbers can be subsequently stored on disk for later analysis, or if the computer is fast enough, processed and displayed in real time. It requires about 200 seconds per MIPS of computer speed to process 100 100-element projections using a backprojection tomographic algorithm and display 10,000 data points (pixels) graphically. Currently, a fast personal computer can do this in less than 10 seconds. Workstation-grade computers are about an order of magnitude faster.

A PREFERRED EMBODIMENT

OPTG 2: Consider a baseline configuration for the OPTG with the following parameters: $R_c=1$ m; $f=R_c/4$; $L_B=20$ cm; $n_p=16$. Accordingly, $R_o$ is 14.3 cm, the temporal separation between pulses is 13.3 ns, and the spatial separation between foci is 2.9 mm. This baseline geometry is capable of generating 40 pulses using a laser beam with a diameter of 5 mm. If fewer than $n_p^{max}/2$ pulses are required, every other pulse can be used, thus halving the length of the cell for a given temporal separation between pulses or doubling the time interval for a given cell size. Further details of this configuration are described in E. J. Beiting, *Appl. Opt.* 31, 2642–2644 (1992).

The OPTG was tested by constructing 1-m ($R_c=102$ cm) and 2-m ($R_c=203$ cm) cells. Mirrors A' and B of each cell were double coated for high reflectivity (r>99% over two wavelength bands (305–350 nm and 490–550 nm). The reflectivity of the output couplers varied between 96.0 and 97.5% across these wavelength intervals. The back of mirror A had a radius of 14.0 cm, yielding paraxial focal lengths of 24 cm ($\approx R_c/4$) for the 1-m cell and 26 cm ($\approx R_c/8$) for the 2-m cell. Diameters of mirrors A and A' were 2.5 cm. Mirror B had a height of 2.5 cm and length of 20 cm. The calculated time separation between pulses for the 1-m and 2-m cells are 13.6 and 27.1 ns, respectively.

Figure 5A:
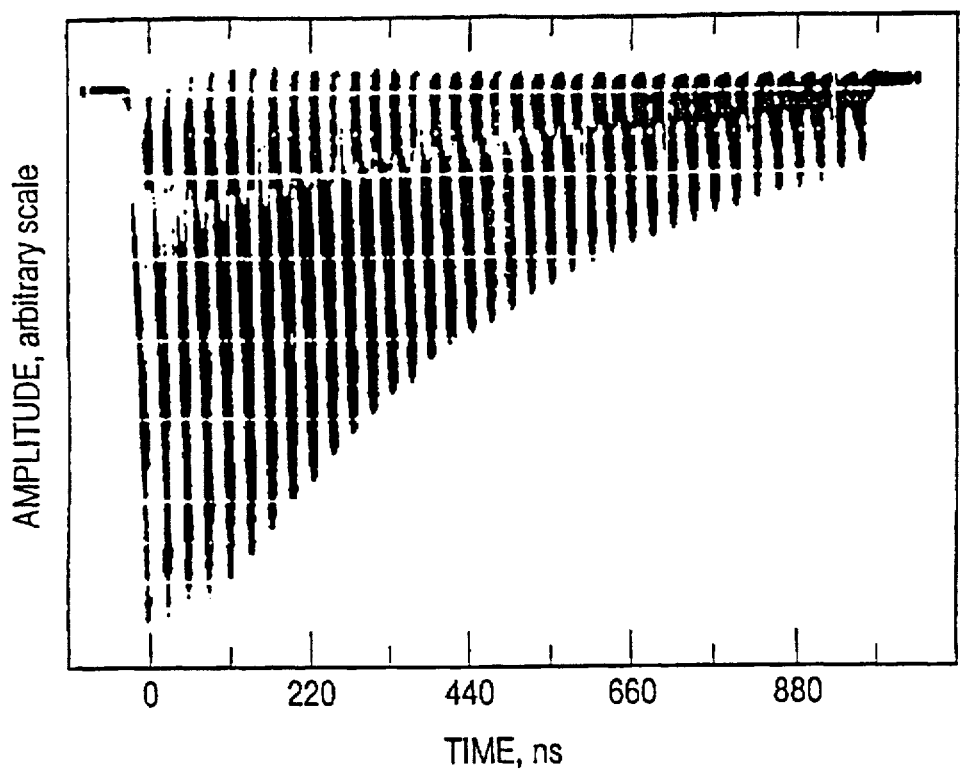
FIG. 5A shows a (negative) pulse train exiting a fast silicon photodiode created by a 2-m OPTG when a variable neutral density filter is not positioned in the expanding fan of output beams.
Figure 5B:
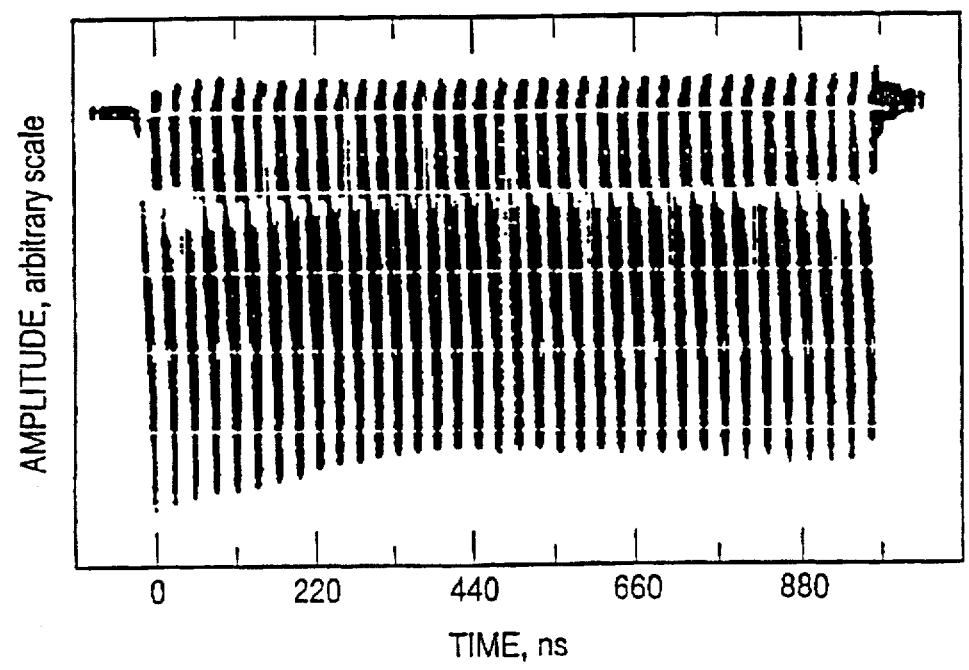
FIG. 5B shows the train when a variable neutral density filter is positioned into the expanding fan of output beams.

These cells performed as expected. FIG. 5 shows oscilloscope traces created by a train of pulses exiting the 2-m cell. Pulsed radiation supplied by the second harmonic output of a Nd:YAG laser was introduced into the cell. A converging lens, placed at the focal plane of the output coupler, focused all the output beams onto a single photodiode with a 1 ns risetime. The 350-MHz-bandwidth oscilloscope measured a pulsewidth of 7.5 ns (FWHM). The 36 pulses shown in the trace span 948 ns and were created over a path length of >280 m. Aperturing the input beam between 2 and 6 mm diameter did not change the relative intensity of the pulses in the train. The ratio of the last-to-first pulse amplitude in FIG. 5A indicates that the reflectivity of the coatings on mirrors B and A' is 0.995 since the measured output-coupler reflectivity is 0.968 at 532 nm. Inserting a neutral density filter that has a linearly varying optical density in the fan of output beams resulted in the trace shown in FIG. 5B. The proper location of the filter was easily identified by coarsely positioning the filter in the fan of output beams while observing the pulse train on the oscilloscope. The spatial separation between the pulses 32.6 cm from the output coupler (near the focal plane) was measured to be 1.0 mm, in agreement with Eq. 2.

Tomography Ring 4

In practice, it will seldom be necessary to require more projection angles than projection elements for artifact-free imaging. Thus, letting $N_f=n_d$, Eqs. 5–7 completely specify the parameters of the instrument for a required flow diameter and resolution. For example, for a 10-cm-diam flow, a resolution of 1 mm, and a fan angle of 30°, we find F=3.86, R=19.32 cm, $\omega=2$ mm, $N_d=606.9$, $n_d=N_f=N_d/N_a=101.15$, and $F_M=16.86$. Of course, $F_M$, $n_d$, $N_f$, and $N_d$ must be integers, and the tabulation given in Table I is useful for identifying the exact configuration for a given application. In the configuration shown in FIG. 4, $n_d=N_f=96$, $F_M=16$, 2r=10.16 cm (4 in.), and R=19.61 cm. Then detector width is given by Eq. 8, viz., $$w = \frac{2(3.14)\left(\frac{10.16\,\text{cm}}{2}\right)}{6(96)} \sqrt{\frac{2}{\left(1-\cos\left(\frac{180°}{6}\right)\right)}} = 0.21\,\text{cm}.$$

This configuration is shown in Table I by bold face type. Silicon photodiodes of greater than 4 mm area that have 1-ns risetimes, and responsivities greater than 0.1 A/W between 190 nm and 1.1 µm are widely available.

An easily replicated fan-beam generator consists of an UV transmitting optical fiber and an optic. Analysis of the capabilities of silica macrofibers for this application [E. J. Beiting, *Appl. Opt.* 31, 1328–1343 (1992)] indicates that the short-wavelength operating limit is limited by this component to 200 nm if a 200-µm-diameter fiber is used. Furthermore, a straightforward spherical-cylindrical lens combination coupled to this fiber produces an intensity profile with highly desirable characteristics. The intensity of an ideal fan varies exponentially as a function of the path length intercepted by a ray within the fan. Accordingly, for a constant absorption coefficient, each detector within the fan will see an equal intensity and the dynamic range will be maximized. Laboratory measurements of the intensity profile produced by this fiber-lens combination closely approximates this ideal. The spherical-cylindrical lens assembly is easily combined into a single micro-optic element.

Electronics 6: The most economical method to digitize the train of pulses emitted from each detector is to use fast sampling techniques and analog shift registers. For example, synchronizing the signal pulses to an 80-MHz clock allows the peak of each 5-ns pulse (separated by 12 ns) to be sampled. Laboratory tests (E. J. Beiting, *Opt. Lett.* 16, 1280 (1991)) using an inexpensive 640-cell integrated circuit confirmed the feasibility of digitizing such a pulse train. Such a system has 40 sets of 16-cell groups available for measurements of temperature, concentration of additional chemical species, fast series of reconstructions, or increased resolution.

Capability of System

To quantify the performance of the tomography ring system, a simplified test instrument was built with the specifications listed above. Here, a single fan beam source and 96 detectors were mounted on a 600 segment of a circle. Each detector was connected to a fast peak-and-hold circuit whose output was fed into a multiplexed 96-channel 12-bit analog-to-digital converter. A flow with a maximum diameter of 10 cm was rotated in the fan beam to create the multiple projections. The fan beam generator comprised a 400-µm-diam silica fiber, a 25 mm f.l. spherical microlens, and a −6.35 mm f.l. cylindrical microlens. Custom designed photodiodes of 2.1-mm width and 2.5 mm height were mounted abutting each other. Details of this device are published in E. J. Beiting, *Appl. Opt.* 31, 1328–1343 (1992).

Figure 6A:
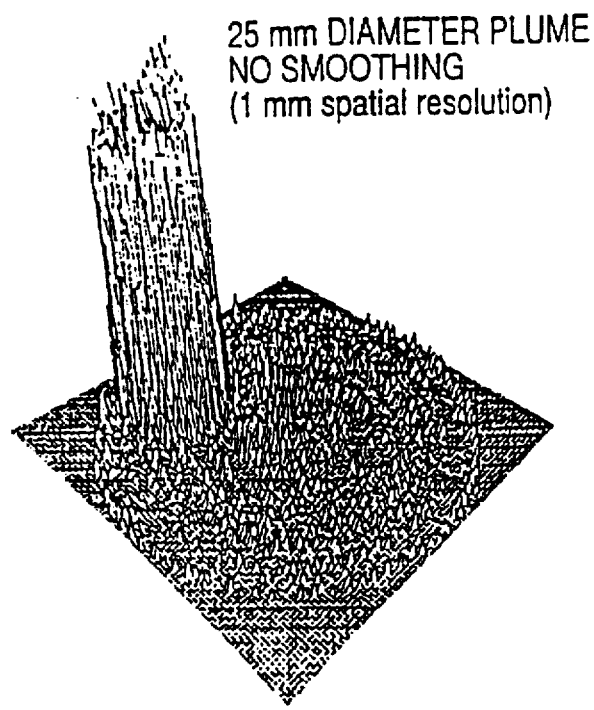
FIG. 6 is a concentration plot of 2.5 cm diameter plume of diacetyl located near the edge of a 10 cm diameter reconstruction zone, where each of the 96 projections was taken using a single pulse of radiation at 444 nm.
Figure 6B:
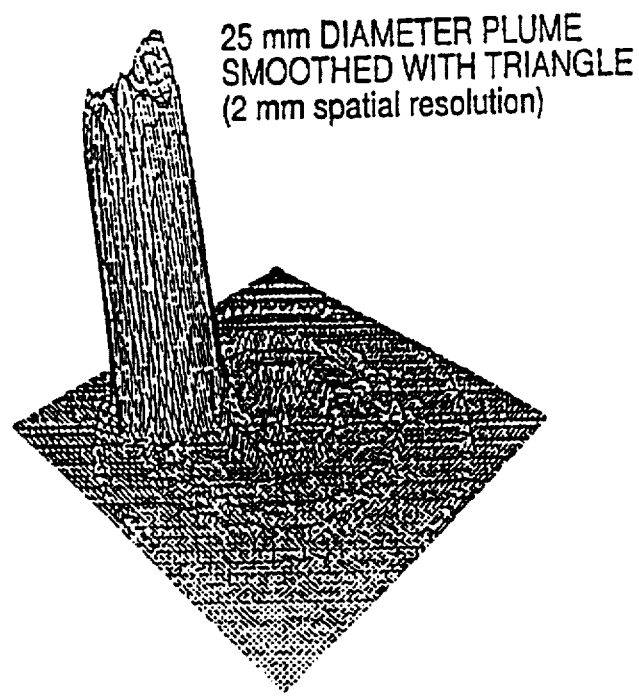

The reconstructions shown in FIG. 6A demonstrate the capability of the system. A boiling flask of diacetyl ($CH_3COCOCH_3$) was rotated in the fan near the edge of the 10-cm diam reconstruction zone. This created an unstable flow with a diameter of 2.5 cm. The average value of the CT numbers in the flow is $6\times10^{-2}$. CT numbers are the unitless product of the absorption coefficient and the pixel length (1.09 mm). The noise both in and out of the flow ($\approx 2.5\times 10^{-3}$) is due to the flow and is not the noise limit of the instrument. The noise in this reconstruction is ~60% greater than that taken when the interprojection noise is largely uncorrelated and more than 400% higher than that taken the interprojection noise is highly correlated (see below.). These noise levels can be reduced further by using spatial averaging as demonstrated in FIG. 6B. The degree of correlation among the projections in the fast instrument depends on the method used to couple the output of the OPTG to the fibers. Simply placing the fibers in the outputs of the OPTG leads to uncorrelated projection noise. Coupling through fused fiber splitters (star couplers) can create correlations that lead to reconstructions with noise values between the correlated and uncorrelated values measured here.

The two principal measures of instrument performance are sensitivity and spatial resolution. Spatial resolution is a function of the number of projections and number of elements within a projection. However, both performance parameters are a function of noise since spatial resolution can be traded for increased sensitivity. Thus reconstruction noise is the principal measure of system performance. Noise in the reconstructed field is a function of the projection noise and the correlation of the noise within a projection.

The principal source of projection noise is due to laser speckle. This noise is caused by shot-to-shot variations in the speckle pattern on the surface of the detectors. The speckle is generate when coherent (laser) light passes through a multimode optical fiber. The speckle is the random pattern created by the constructive and destructive interference among the modes within the fiber. For monochromatic light, there is 100% contrast between light and dark segments; the contrast decreases with increasing bandwidth. Any phenomenon (fiber motion, convective refractive index variations, laser mode stability) that changes the pattern faster than the time required to acquire all of the projections increases the projection noise. The noise is a function of the relative size of the speckle grain to the size of the detector. Fine speckle patterns will generate less noise than coarse grain patterns. The linear dimension of the speckle grain size on the detectors is directly proportional to wavelength and varies inversely with the square of the fiber diameter.

Two types of speckle noise were measured using the test instrument. Stationary speckle noise is the shot-to-shot standard deviation measured when the optical fiber is not purposely moved between laser shots (projections). Dynamic speckle noise is the shot-to-shot standard deviation measured when the fiber is flexed between laser shots. Both types of noise were found to be independent of intensity. These measurements were made using the second harmonic of a Nd:YAG laser that had a stable transverse mode and that could be operated with 1.0 cm$^{-1}$ and 0.003 cm$^{-1}$ bandwidths at 532 nm, and a laser dye oscillator operated at 444 nm that had a very unstable mode.

Table II presents a comparison of the projection noise, linear correlation coefficient which measures the correlation of the noise between detectors within a projection, and reconstruction noise for representative data. The projection noise for the static fiber is highly correlated and its value is considerably less than that measured for the dynamic fiber. Moving the fiber between acquiring the projections largely uncorrelates the data. K. E. Bennett and R. L. Byer, *J. Opt. Soc. Am. A* 3, 624 (1986), presented a careful study of the relationship between the projection noise and reconstruction noise. The last column in Table II lists the ratio of the reconstruction noise measured here with that predicted with their theory for uncorrelated noise. This ratio increases as the correlation coefficient decreases and approaches 1 as the correlation coefficient approaches zero, in agreement with the theory. Correlated projection noise results in less reconstruction noise than uncorrelated projection noise of the same magnitude. The projection noise was found to decrease, and the correlation coefficient increase, with increasing detector size. Thus, increasing the detector size is an effective method of reducing the reconstruction noise caused by speckle.

These noise values in Table II are used to predict the sensitivity of the instrument to a chemical species in a practical environment. For example, consider the hydroxyl radical in an atmospheric pressure flame. Transitions originating from the $F_1$, J=1.5 level are relatively temperature insensitive. The $^PP_{11}$ transition from this level at 308 nm has an effective cross section $q_{\it eff}$ (half the peak value) of 6.9×10$^{-15}$ cm$^2$. For a signal-to-noise ratio of 1, minimum detectivity is $$n_0 = \frac{Q(T)}{g_j \exp(-E_j/kt)} \frac{\sigma_{noise}}{q_{eff}} \quad (9)$$

$$= 5.36 \times 10^{16} \sigma_{noise}(\text{cm}^{-3})$$

where $E_j$ is the energy and $g_j$ is the statistical weight of the level, Q(T) is the partition function, T is temperature, and $\sigma_{noise}$ is the reconstruction noise taken from Table II. The numerical value is calculated for the test geometry and for a flow at a temperature of 1000K. Considering the reduced number density at this temperature in a constant pressure flame, this represents a sensitivity of 5 ppm for the stationary fiber (correlated noise) and 15 ppm for the moving fiber (uncorrelated noise) for a spatial resolution of 1 mm. Increasing the dynamic range of the instrument may be achieved by simultaneously sampling the $^RR_{11}$ transition at 307 nm from the same energy level. This transition has an absorption cross section 30 times less than that of the $^PP_{11}$ transition.

In the fast instrument, a single pulse from a tunable laser is routed to the OPTG to create a series of pulses equally spaced in time. Each of these pulses is subsequently sent to the (six) source positions on the ring that are to be simultaneously activated. If these positions are activated using independent fibers, the projection noise will be largely uncorrelated and the reconstruction noise is approximated by the values measured using the dynamic fiber. If star couplers are used, correlations can be introduced leading to reconstructions with noise values between the static and dynamic values listed in Table II.

The proposed tomography method avoids the problem collisional quenching by measuring the amount of light absorbed directly by $N_0$. By measuring the transmitted light on a linear detector at many angles that are equally spaced around the flow, a cross sectional image of the concentration can be reconstructed using tomographic algorithms. Accordingly, quantitative cross sectional fields of chemical and physical parameters can be reconstructed because the data are straightforward to interpret. Furthermore, tomography has the experimental advantage that optical access outside the plane of observation is not required to collect the data. This is not true for PLIF.

This time-multiplexed design is highly versatile. A single pulse of light introduced into the OPTG will allow the quantitative imaging of the concentration of a chemical species. If a second spectral line is probed by introducing a second pulse into the OPTG at a different wavelength, both the temperature and the concentration of the species can be measured. If this second wavelength is chosen to probe a transition with an absorption cross section differing from that of the first transition by a factor equal to the dynamic range of the concentration achievable using a single wavelength, the dynamic range is increased to the square of the original value. A third sequence of pulses allows the concentration of another species to be measured, etc. Or, the second sequence of pulses can be used to obtain a second "snapshot" of the same species at a later time, thus tracing the time evolution of the flow. Thus the instrument is easily scalable to higher resolution, greater dynamic range, multi-species detection, or to a configuration that allows the temporal development of turbulent structure to be viewed through a series of fast snapshots.

It should be evident to one skilled in the art that many changes and modifications can be made in the configuration or uses of the fast optical tomographic imager without departing from the spirit of the present invention.

TABLE I

| Instrument Parameters[a] | | | |
|---|---|---|---|
| (A) | | | |
| | | d = 10 cm | |
| $\theta_{fan}$ | F | R (cm) | D (cm) |
| 30° | 3.864 | 19.32 | 38.6 |
| 45° | 2.613 | 13.07 | 26.1 |
| 60° | 2.000 | 10.0 | 20.0 |

| (B) | | | | | | | | | | | | |
|---|---|---|---|---|---|---|---|---|---|---|---|---|
| $F_M$ | | | | | | d = 10 cm | | | | | | |
| | $\theta_{fan}$ | | | $N_d$ | | | w (cm)[b] | | | Number of pixels[c] | | |
| $N_f, n_d$ | 30° | 45° | 60° | 30° | 45° | 60° | 30° | 45° | 60° | 30° | 45° | 60° |
| 12 | 2 | 3 | 4 | 72 | 48 | 36 | 1.686 | 1.711 | 1.745 | 141 | 136 | 131 |
| 24 | 4 | 6 | 8 | 144 | 96 | 72 | 0.843 | 0.855 | 0.873 | 563 | 547 | 525 |
| 36 | 6 | 9 | 12 | 216 | 144 | 108 | 0.562 | 0.579 | 0.582 | 1266 | 1230 | 1182 |
| 48 | 8 | 12 | 16 | 288 | 192 | 144 | 0.421 | 0.428 | 0.436 | 2251 | 2186 | 2101 |
| 60 | 10 | 15 | 20 | 360 | 240 | 180 | 0.337 | 0.342 | 0.349 | 3518 | 3416 | 3283 |
| 72 | 12 | 18 | 24 | 432 | 288 | 216 | 0.281 | 0.285 | 0.291 | 5066 | 4920 | 4227 |
| 84 | 14 | 21 | 28 | 504 | 336 | 252 | 0.241 | 0.244 | 0.249 | 6895 | 6696 | 6434 |
| 96 | 16 | 24 | 32 | 576 | 384 | 288 | 0.211 | 0.214 | 0.218 | 8985 | 8746 | 8404 |
| 108 | 18 | 27 | 36 | 648 | 432 | 324 | 0.187 | 0.190 | 0.194 | 11,398 | 11,069 | 10,636 |
| 120 | 20 | 30 | 40 | 720 | 480 | 360 | 0.169 | 0.171 | 0.175 | 14,072 | 13,666 | 13,131 |
| 132 | 22 | 33 | 44 | 792 | 528 | 396 | 0.153 | 0.156 | 0.159 | 17,027 | 16,535 | 15,889 |

[a]The experimental configuration values shown in bold face.
[b]Scales linearly with flow diameter.
[c]Scales quadratically with flow diameter.

TABLE II

System Noise Study

| Conditions | Projection noise (%)[a] | Correlation coefficient | Reconstruction noise × 10³ | Ratio[b] |
|---|---|---|---|---|
| 532 nm, 0.003 cm⁻¹, static fiber | 2.25 (0.4) | 0.6 | 1.4 | 0.93 |
| 532 nm, 1.0 cm⁻¹, static fiber | 2.6 (0.3) | 0.85 | 0.99 | 0.58 |
| 444 nm, 0.5 cm⁻¹, static fiber | 4.0 (0.4) | 0.8–1.0[c] | 0.60 | 0.23 |
| 532 nm, 0.003 cm⁻¹, dynamic fiber | 9.0 (0.5) | 0.1 | 5.4 | 0.90 |
| 532 nm, 1.0 cm⁻¹, dynamic fiber | 7.2 (0.5) | 0.1 | 3.9 | 0.82 |
| 444 nm, 0.5 cm⁻¹, dynamic fiber | 6.0 (0.5) | 0.5 | 1.8 | 0.45 |

[a]Standard deviation of percent projection noise calculated across the fan is presented in parentheses.
[b]Ratio = Measured reconstruction noise/predicted uncorrelated reconstruction noise.
[c]Peaked

I claim:

1. A tomography system for illuminating an absorbing subject, said system comprising pulse means for generating a series of N pulses of light, N fiber optic means for respectively communicating said N pulses, said N fiber optic means respectively comprising N optic inputs respectively receiving said N pulses, said N fiber optic means respectively comprising N splitters for respectively splitting said N optic inputs M times and for connecting each of said N fiber optic inputs to a respective set of M optic outputs of respective N sets of M optic outputs totaling N×M optic outputs angularly circumferentially disposed around said subject in a circle, each of said N sets of M optic outputs are angularly circumferentially offset from each other around said circle, said N fiber optic means for respectively communicating said N pulses from said N optic inputs to said N sets of M optic outputs, each said N optic inputs sequentially respectively communicates one of said N pulses each of which is respectively simultaneously communicated to one of said N sets of said M optic outputs providing a total of N×M pulses, and N×M fan beam generator means each one of which is disposed at a respective end of said N×M optic outputs for respectively receiving said N×M pulses of light and for respectively projecting N×M fan beam pulses illuminating said subject disposed within said circle, said subject absorbing N×M absorbed portions respectively of said N×M fan beam pulses and passing N×M residual portions respectively of said N×M fan beam pulses, N is greater than 1 and M is greater than 1.

2. The system of claim 1 wherein

N equals 16,

M equals 6, said offset is an equiangular 60 degree offset around said circle, and said N×M optic outputs equals 96 equiangularly-disposed every 3.75 degrees around said circle.

3. The tomography system of claim 1 wherein said system further comprises, a plurality of detector means equiangularly circumferentially disposed around in said circle, said plurality of detector means for detecting N×M residual portions of said N×M fan beam pulses of light and for providing detected pulses, each of said plurality of detector means detecting N residual portions of said N×M residual portions of N fan beam pulses of said N×M fan beam pulses projected from a respective circumferential opposing contiguous group of N fan beam generator means of said N×M fan beam generator means, each of said plurality of detector means receives one of said N residual portions from a respective one of said N fan beam pulses projected from a respective one of said N fan beams generator means for a respective one of said N pulses, each of said plurality of detector means for converting said N residual portions respectively into N detected pulses of said detected pulses, a plurality of data acquisition means respectively connected to said plurality of detector means for respectively sampling said N detected pulses for each of said plurality of detector means and for generating residual data, and a data processing means connected to said plurality of data acquisition means for receiving said residual data and for converting said residual data into absorption data of said subject indicating said N×M absorbed portions.

4. The tomography system of claim 1 wherein said series of N pulses are equally spaced in time, said system further comprising, D×M detector means equiangularly circumferentially disposed around in said circle, said D×M detector means for detecting N×M residual portions of said N×M fan beam pulses of light and for providing D×M×N detected pulses, each of N×M residual portions illuminates a respective contiguous group of D detectors of said D×M detectors, each of said D×M detector means detecting N residual portions of said N×M residual portions of N fan beam pulses of said N×M fan beam pulses projected from a respective circumferential opposing contiguous group of N fan beam generator means of said N×M fan beam generator means, each of said D×M detector means receives one of said N residual portions from a respective one of said N fan beam pulses projected from a respective one of said N fan beams generator means for a respective one of said N pulses, each of said D×M detector means for converting said N residual portions respectively into N detected pulses of said D×M×N detected pulses, D×M data acquisition means respectively connected to said D×M detector means for amplitude sampling said D×M×N detected pulses and for generating respective D×M×N residual data for indicating said N×M residual portions, and a data processing means connected to said D×M data acquisition means for receiving said D×M×N residual data and for converting said D×M×N residual data into absorption data of said subject indicating said N×M absorbed portions.

5. The tomography system of claim 4 wherein said circle is defined by any one of N sets of M arcs of circumferentially overlapping N×M arcs disposed around said circle, each of said N sets of M arcs are equiangularly circumferentially offset from each other around said circle, each of said N×M arcs are equal in radians, D detectors of said D×M detectors are equiangularly circumferentially disposed in each of said M arcs of said N×M arcs.

6. The tomography system of claim 4 wherein each of said series of N pulses are generated within 196 ns, D equals 96, N equals 16, and M equals 6.

7. A method for determining the absorption data of a flow of turbulent gas in a tomographic ring, said method comprising the steps of, generating repetitively a pulse as a series of N pulses of light each of which having an identical shape and a proportional amplitude to each other, transmitting said pulse of said series of N pulses to a respective one of N optic inputs, communicating said pulse of said series of N pulses from said respective one of said N optic inputs to a respective set of M optic outputs of N sets of M optical outputs angularly circumferentially disposed on said ring, each of said N sets of M optic outputs angularly circumferentially offset from each other on said ring, illuminating said gas simultaneously by respective M fan beams of N×M fan beams angularly circumferentially generated on said ring from said pulse by simultaneously projecting said pulse from said respective set of M optic outputs, detecting angularly circumferentially said pulse on said ring D simultaneous times for each of said M fan beams after passing through said gas, sampling amplitudes of said pulse D times for each of said M fan beams to acquire simultaneous D×M residual data, repeating said transmitting, communicating, illuminating, detecting, and sampling steps N times in sequence for each of said series of N pulses to generate D×M×N residual data, and processing said D×M×N residual data for determining said absorption data of said gas, N is greater than 1 and M is greater than 1.

8. The method of claim 7 wherein said method further comprising the step of, vacating said gas from said ring, calibrating said system by executing said generating, communicating, illuminating, detecting, sampling and repeating steps, said D×M×N residual data is calibration data when said ring is vacated, and storing said calibration data, said processing step further processing said calibration data for providing a calibration reference for said D×M×N residual data generated when said gas is within said ring.

9. The method of claim 7 wherein said method further comprises the step of, synchronizing said sampling step to said generation step for acquiring said D×M residual data time referenced to said pulse.

10. The method of claim 7 wherein said method further comprises the step of, attenuating said proportional amplitude of said pulse to a constant amplitude.

* * * * *